United States Patent [19]

Hazato et al.

[11] Patent Number: 5,530,027
[45] Date of Patent: Jun. 25, 1996

[54] EXTERNAL SKIN TREATMENT AGENT COMPOSITION CONTAINING PROSTACYCLINS AS ACTIVE INGREDIENT

[75] Inventors: Atsuo Hazato; Nobuaki Hanajima; Yuji Makino, all of Hino; Toshiaki Takeda, Narashino; Tamotsu Koyama, Hachioji, all of Japan

[73] Assignee: Teijin Limited, Osaka, Japan

[21] Appl. No.: 313,147

[22] PCT Filed: Feb. 3, 1994

[86] PCT No.: PCT/JP94/00164

§ 371 Date: Oct. 3, 1994

§ 102(e) Date: Oct. 3, 1994

[87] PCT Pub. No.: WO94/17806

PCT Pub. Date: Aug. 18, 1994

[30] Foreign Application Priority Data

Feb. 3, 1993 [JP] Japan .................. 5-016318

[51] Int. Cl.[6] ................. A61K 31/215
[52] U.S. Cl. ................. 514/530; 514/573
[58] Field of Search ................. 514/530, 573

[56] References Cited

U.S. PATENT DOCUMENTS

| | | | |
|---|---|---|---|
| 4,699,921 | 10/1987 | Shibasaki et al. | 514/530 |
| 4,705,806 | 11/1987 | Morton, Jr. | 514/530 |
| 5,364,883 | 11/1994 | Bannai et al. | 514/530 |
| 5,380,760 | 1/1995 | Wendel et al. | 514/573 |
| 5,464,868 | 11/1995 | Frölich et al. | 514/530 |

FOREIGN PATENT DOCUMENTS

| | | |
|---|---|---|
| 0015658 | 9/1980 | European Pat. Off. . |
| 3704825 | 8/1988 | Germany . |
| 4164034 | 6/1992 | Japan . |

OTHER PUBLICATIONS

Mizushima et al, *J. of Controled Release*, 28:243–249 (1994).

*Primary Examiner*—José G. Dees
*Assistant Examiner*—Barbara S. Frazier
*Attorney, Agent, or Firm*—Sughrue, Mion, Zinn, Macpeak & Seas

[57] ABSTRACT

An external skin treatment agent composition containing an active ingredient comprising of a prostacyclin, and/or its optical isomer, having the formula (I):

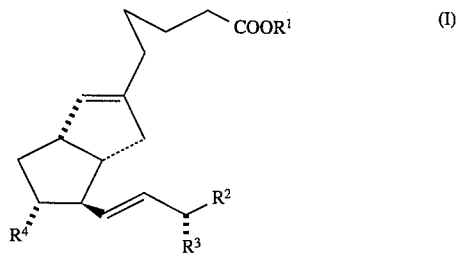

(wherein, $R^1$ is a hydrogen atom, a straight chain or branched alkyl group of $C_1$ to $C_{10}$, or one equivalent of cations, $R^2$ is $-(CH_2)_2R^{21}$ or a substitutable $C_3$ to $C_{10}$ cycloalkyl group, where $R^{21}$ is a substitutable $C_1$ to $C_{10}$ straight chain or branched alkyl group or substitutable $C_2$ to $C_{10}$ straight chain or branched alkenyl group or alkynyl group, and $R^3$ and $R^4$ are independently a hydroxyl group or formula $$-OCR^5_{\parallel} \atop O$$

(wherein, $R^5$ is a $C_1$ to $C_5$ straight chain or branched alkyl group)) and a carrier.

19 Claims, 1 Drawing Sheet

CHANGES IN AMOUNT OF BLOOD FLOW OF SKIN TREATED BY DOSE OF VASELINE OINTMENT CONTAINING SPECIMEN (THREE CONCENTRATIONS)(HAIRLESS RATS)
DOSAGE: 23 mg/4.5 cm$^2$
TREATED PORTION: THIGH (DEPILATED, OPEN SYSTEM)
BLOOD FLOWMETER: LASER FLOWMETER (ADVANCE CO., LTD.)

● ; 40.0 μg/g
▲ ; 20.0 μg/g
■ ; 10.0 μg/g
○ ; Placebo

EXTERNAL SKIN TREATMENT AGENT COMPOSITION CONTAINING PROSTACYCLINS AS ACTIVE INGREDIENT

TECHNICAL FIELD

The present invention relates to an external skin treatment agent composition. More specifically, it relates to an external skin treatment agent composition containing a prostacyclin derivative as an active ingredient.

BACKGROUND ART

Prostaglandins are compounds which have diverse physiological actions such as a powerful action in suppressing blood platlet aggregation, action in reducing the vasodilation blood pressure, action in suppressing gastric acid secretion, smooth muscle contraction action, cell protection action, and diuretic action and is useful for the treatment or prevention of myocardial infarct, cardiac angina, arteriosclerosis, hypertension, duodenal ulcers, induced parturition, abortion, etc.

On the other hand, in recent years, there has been a tendency toward an increase of skin ulcers, in particular, the decubitus ulcers known commonly as bedsores, along with the higher age of the subjects being treated for various ailments. For example, about 5% of the approximately 12 million senior citizens in Japan today, or 600,000 people, are bed-ridden. These people are said to suffer from decubitus ulcers at a high frequency. In the past, the treatment for skin ulcers, including decubitus ulcers, consisted of improvement of local conditions using antibiotics, antibacterial agents, ointments containing enzymes etc., skin cleaning solutions, or water absorbing polymer powders, wound covering agents, etc. These have been tried along with removal and mitigation of the pressure on the diseased sites, surgical debridement for removal of the destroyed tissue, treatment of systemic conditions by transfusions, intraintestinal nutrition, and IVH, but these treatments still cannot be said to be sufficiently effective. On the other hand, attempts have been made to apply prostaglandin E, prostaglandin F, and prostaglandin $I_1$ transdermal preparations to skin ulcers, including decubitus ulcers, for the purpose of improvement of skin ulcers by application to local areas, but the stability of the main medication, the release of the main medication from the ointment, the stimulus to the skin, and the efficacy have not always necessarily met clinical requirements.

Natural prostacyclin, however, is a local hormone produced mainly by the hemangioendothelium in the body. Attempts have been made to make use of its powerful physiological activity, for example, its activity in suppressing aggregation of blood platlets, its vasodilation activity, etc. to use the same as a direct pharmaceutical (P. J. Lewis, J. O. Grady, Clinical Pharmacology of Prostaglandin). Natural prostacyclin, however, contains an enol-ether bond which is extremely easily hydrolyzed in the molecules, and therefore, easily loses its activity under neutral or acidic conditions. Accordingly, it cannot be said to be a desirable compound as a pharmaceutical due to its chemical instability. Therefore, intensive research has been carried out on synthesizing a synthetic prostacyclin which has a similar physiological activity as natural prostacyclin and is chemically stable (Synthesis, 1984, 449). The present inventors succeeded in synthesizing the prostacyclin analogs, which are 9(O)-methano-$\Delta^{6(9\alpha)}$-prostaglandins $I_2$ (isocarbacyclin), derivatives which are sufficiently satisfactory in the chemical stability, by replacing oxygen atoms at the 6(9$\alpha$)-position of prostacyclin with the methine group (—CH=) (see Japanese Unexamined Patent Publication (Kokai) No. 59-210044). This derivative has physiological activity, such as a powerful action in inhibitory effect on aggregation of blood platlets and an action in reducing the blood pressure, comparable with natural prostacyclin and is useful for cardiovascular system (see Japanese Unexamined Patent Publication (Kokai) Nos. 59-210044 and 61-197518).

DISCLOSURE OF THE INVENTION

The present inventors took note of the powerful activity in suppressing aggregation of blood platlets and vasodilation action of stabilized prostacyclin derivatives (isocarbacyclins) and engaged in intensive studies on the possibilities of it as an external skin treatment agent such as an agent for treatment of skin ulcers, including decubitus ulcers, and as a result, found activity suggesting that possibility in isocarbacyclin in the present invention and thereby reached the present invention.

That is, in accordance with the present invention, there is provided an external skin treatment agent composition containing an active ingredient comprising a prostacyclin, and/or its optical isomer, having the formula (I):

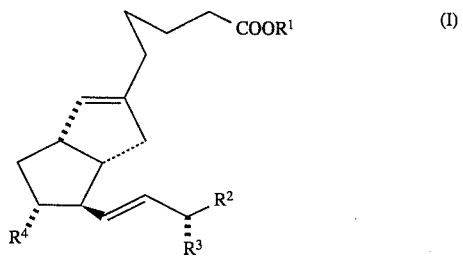

(wherein, $R^1$ is a hydrogen atom, a straight chain or branched alkyl group of $C_1$ to $C_{10}$, or one equivalent of a cation, $R^2$ is $-(CH_2)_2R^{21}$ or a substitutable $C_3$ to $C_{10}$ cycloalkyl group, where $R^{21}$ is a substitutable $C_1$ to $C_{10}$ straight chain or branched alkyl group or substitutable $C_2$ to $C_{10}$ straight chain or branched alkenyl group or alkinyl group, and $R^3$ and $R^4$ are independently a hydroxyl group or formula:

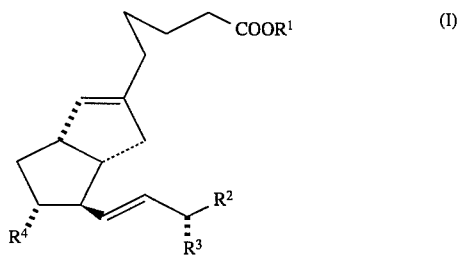

(wherein, $R^5$ is a $C_1$ to $C_5$ straight chain or branched alkyl group)) and a carrier.

BEST MODE FOR CARRYING OUT THE INVENTION

Figure 1:
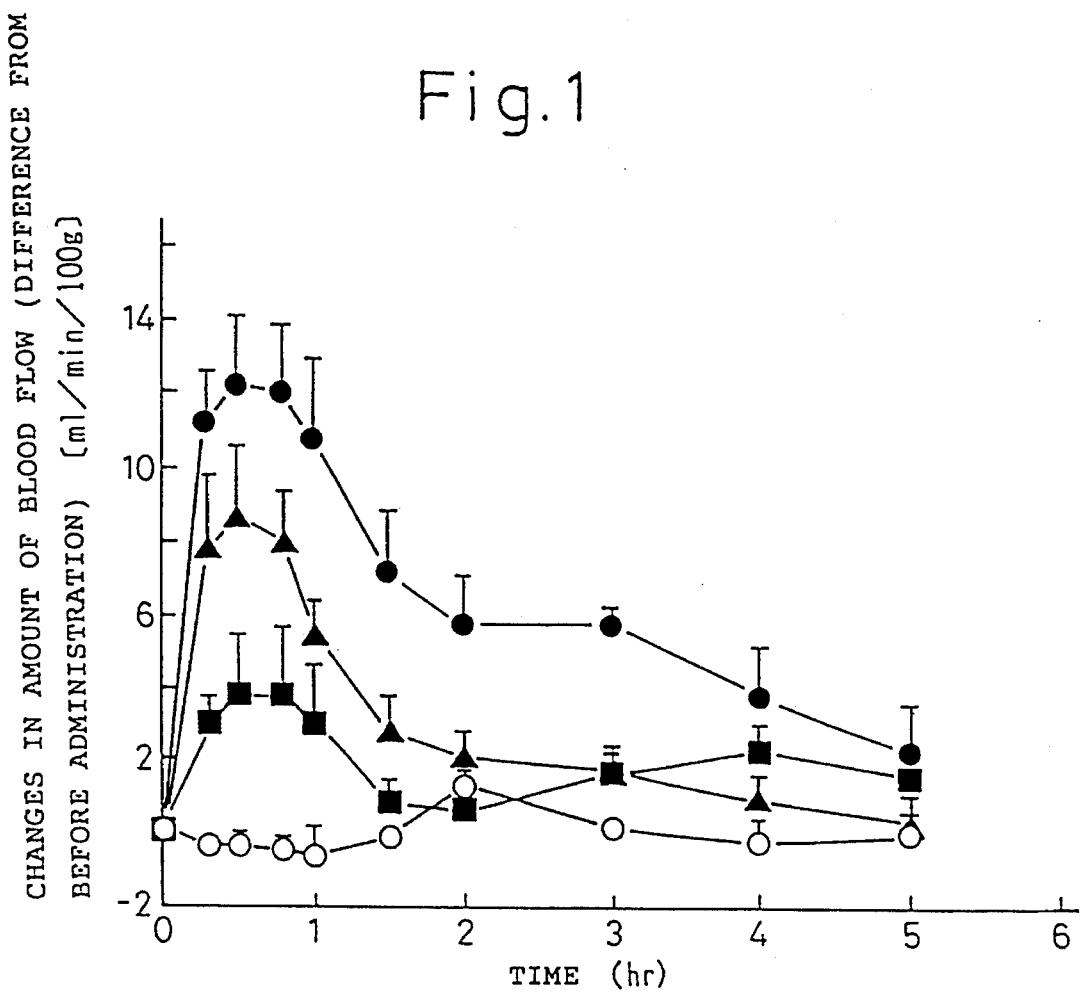
FIG. 1 is a graph of the effect of increasing the flow of blood at the skin by to the external skin treatment composition agent composition of the present invention.

In formula (I), $R^1$ is a hydrogen atom, a $C_1$ to $C_{10}$ straight chain or branched alkyl group, or one equivalent weight of cations. As the $C_1$ to $C_{10}$ alkyl group, mention may be made, for example, of a methyl group, ethyl group, n-propyl group, iso-propyl group, n-butyl group, sec-butyl group, tert-butyl group, n-pentyl group, n-hexyl group, n-heptyl group, n-octyl group, n-nonyl group, n-decyl group, etc. Among these, a $C_1$ to $C_6$ alkyl group, in particular, a $C_1$ to $C_4$ alkyl group, is preferable. As the one equivalent weight of cations, mention may be made for example of alkali metal cations such as $Na^+$, $K^+$; bivalent or trivalent metal cations such as $\frac{1}{2}Ca^{2+}$, $\frac{1}{2}Mg^{2+}$, $\frac{1}{3}Al^{3+}$; and ammonium cations such as ammonium ions, tetramethyl ammonium ions. As $R^1$, a hydrogen atom or methyl group are particularly preferred, more particularly a methyl group is preferred.

In formula (I), $R^2$ is $-(CH_2)_2R^{21}$ or a substitutable $C_3$ to $C_{10}$ cycloalkyl group. Here, $R^{21}$ is a substitutable $C_1$ to $C_{10}$ straight chain or branched alkyl group or substitutable $C_2$ to $C_{10}$ straight chain or branched alkenyl group or alkinyl group. As the unsubstituted $C_1$ to $C_{10}$ alkyl group related to $R_{21}$, mention may be made for example of a methyl group, ethyl group, n-propyl group, iso-propyl group, n-butyl group, sec-butyl group, tert-butyl group, n-pentyl group, 2-methylbutyl-4-yl group, 3-methylbutyl- 4-yl group, 4-methylbutyl-4-yl group, n-hexyl group, 2-methylpentyl-5-yl group, 3-methylpentyl-5-yl group, 4-methylpentyl-5-yl group, 5-methylpentyl-5-yl group, n-heptyl group, 2-methylhexyl-6-yl group, 3-methylhexyl- 6-yl group, 4-methylhexyl-6-yl group, 5-methylhexyl- 6-yl group, 6-methylhexyl-6-yl group, etc. Among these, a $C_1$ to $C_8$ alkyl group, in particular a $C_5$ to $C_8$ alkyl group, is preferred.

Further, as the unsubstituted $C_2$ to $C_{10}$ alkenyl group relating to $R^{21}$, mention may be made for example of a 1-methylvinyl group, vinyl group, 1-propenyl group, 1-butenyl group, 1-pentenyl group, 1-hexenyl group, 1-heptenyl group, allyl group, methallyl group, 2-butenyl group, 2-pentenyl group, 2-hexenyl group, 2-heptenyl group, 1-pentene-2-yl group, 3-methyl-1-butene-1-yl group, 3-methyl-1-pentene-1-yl group, 4-methyl-1-pentene- 1-yl group, 3-methyl-1-hexene-1-yl group, 4-methyl-1-hexene- 1-yl group, 3-methyl-1-heptene-1-yl group, 5-methyl- 1-heptene-1-yl group, 3,3-dimethyl-1-heptene-1-yl group, 2-pentene-3-yl group, 3-methyl-2-butenyl group, 4-methyl- 2-pentenyl group, 4-methyl-2-hexenyl group, 5-methyl- 2-heptenyl group, 4,4-dimethyl-2-hexenyl group, 1-butene- 4-yl group, 2-methyl-1-butene-4-yl group, 3-methyl- 1-butene-4-yl group, 2-pentene-4-yl group, 3-hexenyl group, 3-heptenyl group, 3,3-dimethyl-1-butene-4-yl group, 1-pentene-5-yl group, 4-methyl-pentene-5-yl group, 4,4-dimethyl-pentene-5-yl group, 3-methyl-pentene- 5-yl group, 2-methyl-pentene-5-yl group, 2-hexene-6-yl group, 2-methyl-2-hexene-6-yl group, 5-methyl-2-hexene-6-yl group, 5,5-dimethyl-2-hexene-6-yl group, 4-ethyl-3-hexenyl group, 4-methyl-3-hexenyl group, 2-methyl-2-pentene group, 2-methyl-3-hexenyl group, 5-methyl-3-hexenyl group, 2-methyl-3-heptenyl group, 6-methyl-3-heptenyl group, 2,5-dimethyl-2-hexene-6-yl group, 2-methyl- 2-heptene-6-yl group, 2,6-dimethyl-2-heptene-6-yl group, 3-heptene-7-yl group, 3-methyl-heptene-7-yl group, 3-ethyl-heptene-7-yl group, 5-methyl-heptene-7-yl group, 6-methyl-heptene-7-yl group, 6,6-dimethyl-heptene-7-yl group, etc. Among these, a $C_2$ to $C_8$ alkenyl group, in particular a $C_5$ to $C_8$ alkenyl group, is preferable.

Further, as the unsubstituted $C_2$ to $C_{10}$ alkynyl group relating to the $R^{21}$, mention may be made for example of an ethynyl group, 1-propine-3-yl group, butynyl group, pentynyl group, hexynyl group, heptynyl group, 3-methyl-butynyl group, 3,3-dimethyl-butynyl group, 3-methyl-pentynyl group, 3,3-dimethyl-pentynyl group, 3-ethyl-pentynyl group, 4-methyl-pentynyl group, 4,4-dimethyl-pentynyl group, 3-methyl-hexynyl group, 3,3-dimethyl-hexynyl group, 5-methyl-hexynyl group, 5,5-dimethyl-hexynyl group, 3-methyl-heptynyl group, 3,3-dimethyl-heptynyl group, 5-methyl-heptynyl group, 5-ethyl-heptynyl group, 5,5-dimethyl-heptynyl group, 1-propine-3-yl group, 1-butine-3-yl group, 2-pentine-3-yl group, 2-butine-1-yl group, 2-pentine-1-yl group, 4-methyl-2-pentine-1-yl group, 4,4-dimethyl-2-pentine-1-yl group, 2-hexine-1-yl group, 4-methyl-2-hexine-1-yl group, 4-ethyl-2-hexine-1-yl group, 4,4-dimethyl-2-hexine-1-yl group, 2-heptine-1-yl group, 3-octine-2-yl group, 4-methyl-2-heptine-1-yl group, 4,4-dimethyl-2-heptine-1-yl group, 5,5-dimethyl-2-heptine- 1-yl group, 5-ethyl-2-heptine-1-yl group, 3-heptine- 2-yl group, 1-butine-4-yl group, 1-pentine-4-yl group, 3-methyl-1-butine-4-yl group, 2-pentine-5-yl group, 3-hexine-1-yl group, 5-methyl-3-hexine-1-yl group, 2-methyl-3-hexine-1-yl group, 5,5-dimethyl-3-hexine-1-yl group, 2,2-dimethyl-3-hexine-1-yl group, 3-heptine-1-yl group, 4-octine-2-yl group, 2-methyl-4-octine-2-yl group, 2,2-dimethyl-3-heptine-1-yl group, 2-methyl-3-heptine-1-yl group, 5-methyl-3-heptine-1-yl group, 2-hexine-5-yl group, 5-ethyl-3-heptine-1-yl group, 6-methyl-3-heptine- 1-yl group, 6,6-dimethyl-3-heptine-1-yl group, 1-pentine- 5-yl group, 1-hexine-5-yl group, 4-methyl-1-pentine-5-yl group, 4,4-dimethyl-1-pentine-5-yl group, 3-methyl-1-pentine- 5-yl group, 3,3-dimethyl-1-pentine-5-yl group, 2-hexine-6-yl group, 2-heptine-6-yl group, 5-methyl-2-hexine- 6-yl group, 5,5-dimethyl-2-hexine-6-yl group, 4-methyl- 2-hexine-6-yl group, 4,4-dimethyl-2-hexine-6-yl group, 3-heptine-7-yl group, 3-octine-7-yl group, 6-methyl- 3-heptine-7-yl group, 6,6-dimethyl-3-heptine-7-yl group, 5-methyl-3-heptine-7-yl group, 2-methyl-3-heptine- 7-yl group, 2,2-dimethyl-3-heptine-7-yl group, 1-hexine- 6-yl group, 1-heptine-6-yl group, 6-methyl-1-heptine-6-yl group, 5-methyl-1-hexine-6-yl group, 5,5-dimethyl-1-hexine- 6-yl group, 4-methyl-1-hexine-6-yl group, 3-methyl- 1-hexine-6-yl group, 3,3-dimethyl-1-hexine-6-yl group, 2-heptine-7-yl group, 2-octine-7-yl group, 7-methyl-2-octine-7-yl group, 5,5-dimethyl-2-heptine-7-yl group, 4-methyl-2-heptine-7-yl group, 4,4-dimethyl-2-heptine-7-yl group, 1-heptine-7-yl group, 1-octine-7-yl group, 7-methyl-1-octine-7-yl group, 5-methyl-1-heptine- 7-yl group, 4-methyl-1-heptine-7-yl group, 3-methyl-1-heptine- 7-yl group, 3,3-dimethyl-1-heptine-7-yl group, 4,4-dimethyl-1-heptine-7-yl group, etc. Among these, a $C_2$ to $C_8$ alkenyl group, in particular a $C_5$ to $C_8$ alkenyl group, is preferred.

As the $R^{21}$ substituent groups, mention may be made of halogen atoms such as fluorine, chlorine, lower alkoxy groups such as, a methoxy group, ethoxy group, propoxy group, butoxy group, such as cyclopentyl group, cyclohexyl group, $C_3$ to $C_8$ cycloalkyl groups. Among these, a lower alkoxy group or cycloalkyl group is preferred.

In the $-(CH_2)_2R^{21}$ relating to $R^2$ in the formula (I), $R^{21}$ is preferably a $C_1$ to $C_5$ straight chain or branched alkyl group. As the $C_1$ to $C_5$ alkyl group, mention may be made for example of a methyl group, ethyl group, n-propyl group, iso-propyl group, n-butyl group, sec-butyl group, tert-butyl group, n-hexyl group, etc. Among these, as the $R^{21}$, a $C_3$ to $C_5$ alkyl group is preferred, more preferably an n-propyl group or n-butyl group, particularly preferably an n-propyl group.

As specific examples of the cycloalkyl group in the case where the $R^2$ relating to formula (I) is a substitutable $C_3$ to $C_{10}$ cycloalkyl group, mention may be made of a cyclopentyl group, a cyclohexyl group, etc. In particular, a $C_3$ to $C_8$ cycloalkyl group, in particular a $C_4$ to $C_7$ cycloalkyl group, is preferable. It should be noted that as the substituent group, mention may be made, for example, of $C_1$ to $C_6$ lower alkyl group such as a methyl group, ethyl group, propyl group, hexyl group, a halogen atom such as a fluorine, chlorine, lower alkoxyl groups, such as a methoxy group, ethoxy group, propoxy group, butoxy group, halogenated lower alkyl group, such as a trifluoromethyl group.

As the $R^2$ in formula (I), mention may be made of $-(CH_2)_2R^{21}$ as a preferable example.

In formula (I), $R^3$ and $R^4$ are independently, that is, the same or differently, a hydroxyl group or the formula:

Here, $R^5$ is a $C_1$ to $C_5$ straight chain or branched alkyl group, for example, mention may be made of those similar to the examples of $R^2$. As the $R^5$, a $C_1$ to $C_3$ alkyl group is preferable, in particular a straight chain one. It should be noted that as $R^5$, a methyl group is particularly preferred. Further, as the $R^3$ and $R^4$, a hydroxyl group is particularly preferable.

The prostacyclins expressed in formula (I) with configurations of the 8-, 9-, 11-, 12-, and 15-positions the same as natural prostacyclins are a particularly useful sterioisomer, but the present invention includes the stereoisomers resulting from different configurations thereof and any combinations thereof.

Preferable specific examples of the prostacyclin usable in the present invention are as follows:

(1) 9(O)-methano-$\Delta^{6(9\alpha)}$-prostaglandin $I_1$
(2) 20-methyl-9(O)-methano-$\Delta^{6(9\alpha)}$-prostaglandin $I_1$
(3) 19,20-dinol-9(O)-methano-$\Delta^{6(9\alpha)}$-prostaglandin $I_1$
(4) 20-nol-9(O)-methano-$\Delta^{6(9\alpha)}$-prostaglandin $I_1$
(5) 19 -methyl-9(O)-methano-$\Delta^{6(9\alpha)}$-prostaglandin $I_1$
(6) 18-methyl-9(O)-methano-$\Delta^{6(9\alpha)}$-prostaglandin $I_1$
(7) 20-ethyl-9(O)-methano-$\Delta^{6(9\alpha)}$-prostaglandin $I_1$
(8) 20-isopropyl-9(O)-methano-$\Delta^{6(9\alpha)}$-prostaglandin $I_1$
(9) 20-methyl-20-ethyl-9(O)-methano-$\Delta^{6(9\alpha)}$-prostaglandin $I_1$
(10) 19-methyl-20-ethyl-9(O)-methano-$\Delta^{6(9\alpha)}$-prostaglandin $I_1$
(11) 18-methyl-20-ethyl-9(O)-methano-$\Delta^{6(9\alpha)}$-prostaglandin $I_1$
(12) 20-propyl-9(O)-methano-$\Delta^{6(9\alpha)}$-prostaglandin $I_1$
(13) 22-methyl-20-propyl-9(O)-methano-$\Delta^{6(9\alpha)}$-prostaglandin $I_1$
(14) 21-methyl-20-propyl-9(O)-methano-$\Delta^{6(9\alpha)}$-prostaglandin $I_1$
(15) 20-methyl-20-propyl-9(O)-methano-$\Delta^{6(9\alpha)}$-prostaglandin $I_1$
(16) 19-methyl-20-propyl-9(O)-methano-$\Delta^{6(9\alpha)}$-prostaglandin $I_1$
(17) 18-methyl-20-propyl-9(O)-methano-$\Delta^{6(9\alpha)}$-prostaglandin $I_1$
(18) 20-nol-18-methylene-9(O)-methano-$\Delta^{6(9\alpha)}$-prostaglandin $I_1$
(19) 20-nol-18,19-dehydro-9(O)-methano-$\Delta^{6(9\alpha)}$-prostaglandin $I_1$
(20) 18,19-dehydro-9(O)-methano-$\Delta^{6(9\alpha)}$-prostaglandin $I_1$
(21) 18,19-dehydro-20-methyl-9(O)-methano-$\Delta^{6(9\alpha)}$-prostaglandin $I_1$
(22) 18,19-dehydro-20-ethyl-9(O)-methano-$\Delta^{6(9\alpha)}$-prostaglandin-$I_1$
(23) 18,19-dehydro-20-propyl-9(O)-methano-$\Delta^{6(9\alpha)}$-prostaglandin $I_1$
(24) 18,19-dehydro-20-butyl-9(O)-methano-$\Delta^{6(9\alpha)}$-prostaglandin $I_1$
(25) 18-methylene-20-methyl-9(O)-methano-$\Delta^{6(9\alpha)}$-prostaglandin $I_1$
(26) 18,19-dehydro-20,20-dimethyl-9(O)-methano-$\Delta^{6(9\alpha)}$-prostaglandin $I_1$
(27) 18,19-dehydro-20-methyl-20-ethyl-9(O)-methano-$\Delta^{6(9\alpha)}$-prostaglandin $I_1$
(28) 18,19-dehydro-20-isopropyl-20-ethyl-9(O)-methano-$\Delta^{6(9\alpha)}$-prostaglandin $I_1$
(29) 18,19-dehydro-20-methyl-20-butyl-9(O)-methano-$\Delta^{6(9\alpha)}$-prostaglandin $I_1$
(30) 18,19-dehydro-20-(1-methylpropyl)-9(O)-methano-$\Delta^{6(9\alpha)}$-prostaglandin $I_1$
(31) 18,19-dehydro-20-methyl-20-propyl-9(O)-methano-$\Delta^{6(9\alpha)}$-prostaglandin $I_1$
(32) 18,19-dehydro-20,20-dimethyl-20-butyl-9(O)-methano-$\Delta^{6(9\alpha)}$-prostaglandin $I_1$
(33) 19,20-dehydro-9(O) -methano-$\Delta^{6(9\alpha)}$-prostaglandin $I_1$
(34) 19,20-dehydro-20-methyl-9(O)-methano-$\Delta^{6(9\alpha)}$-prostaglandin $I_1$
(35) 19,20-dehydro-19-methyl-9(O)-methano-$\Delta^{6(9\alpha)}$-prostaglandin $I_1$
(36) 19,20-dehydro-20-ethyl-9(O)-methano-$\Delta^{6(9\alpha)}$-prostaglandin $I_1$
(37) 19,20-dehydro-20-propyl-9(O)-methano-$\Delta^{6(9\alpha)}$-prostaglandin $I_1$
(38) 19,20-dehydro-20-butyl-9(O)-methano-$\Delta^{6(9\alpha)}$-prostaglandin $I_1$
(39) 19,20-dehydro-18,20-dimethyl-9(O)-methano-$\Delta^{6(9\alpha)}$-prostaglandin $I_1$
(40) 19,20-dehydro-20-(1-methylpropyl)-9(O)-methano-$\Delta^{6(9\alpha)}$-prostaglandin $I_1$
(41) 19,20-dehydro-20-isopropyl-9(O)-methano-$\Delta^{6(9\alpha)}$-prostaglandin $I_1$
(42) 19,20-dehydro-20-(2-methylbutyl)-9(O)-methano-$\Delta^{6(9\alpha)}$-prostaglandin $I_1$
(43) 19,20-dehydro-20-(1,1-dimethylpropyl)-9(O)-methano-$\Delta^{6(9\alpha)}$-prostaglandin $I_1$
(44) 20-methylene-9(O)-methano-$\Delta^{6(9\alpha)}$-prostaglandin $I_1$
(45) 20-methyl-20-methylene-9(O)-methano-$\Delta^{6(9\alpha)}$-prostaglandin $I_1$
(46) 19-methyl-20-methylene-9(O)-methano-$\Delta^{6(9\alpha)}$-prostaglandin $I_1$
(47) 20-ethylidene-9(O)-methano-$\Delta^{6(9\alpha)}$-prostaglandin $I_1$
(48) 20-propylidene-9(O)-methano-$\Delta^{6(9\alpha)}$-prostaglandin $I_1$
(49) 20-butylidene-9(O)-methano-$\Delta^{6(9\alpha)}$-prostaglandin $I_1$
(50) 20-(1-ethylbutylidene)-9(O)-methano-$\Delta^{6(9\alpha)}$-prostaglandin $I_1$
(51) 20-(1-methylbutylidene)-9(O)-methano-$\Delta^{6(9\alpha)}$-prostaglandin $I_1$
(52) 20-(1-methylethylidene)-9(O)-methano-$\Delta^{6(9\alpha)}$-prostaglandin $I_1$
(53) 19-methyl-20-propylidene-9(O)-methano-$\Delta^{6(9\alpha)}$-prostaglandin $I_1$
(54) 20-(2-methylpropylidene)-9(O)-methano-$\Delta^{6(9\alpha)}$-prostaglandin $I_1$
(55) 19-methyl-20-butylidene-9(O)-methano-$\Delta^{6(9\alpha)}$-prostaglandin $I_1$
(56) 20-(3-methylbutylidene)-9(O)-methano-$\Delta^{6(9\alpha)}$-prostaglandin $I_1$
(57) 19 19-dimethyl-20-methylene-9(O)-methano-$\Delta^{6(9\alpha)}$-prostaglandin $I_1$
(58) 20-vinyl-9(O)-methano-$\Delta^{6(9\alpha)}$-prostaglandin $I_1$
(59) 19-methyl-20-vinyl-9(O)-methano-$\Delta^{6(9\alpha)}$-prostaglandin $I_1$
(60) 19,19-dimethyl-20-vinyl-9(O)-methano-$\Delta^{6(9\alpha)}$-prostaglandin $I_1$
(61) 20-methyl-20-vinyl-9(O)-methano-$\Delta^{6(9\alpha)}$-prostaglandin $I_1$
(62) 20-(1-methylvinyl)-9(O)-methano-$\Delta^{6(9\alpha)}$-prostaglandin $I_1$

(63) 20-(1-propenyl)-9(O)-methano-$\Delta^{6(9\alpha)}$-prostaglandin $I_1$
(64) 20-(2-methyl-1-propenyl)-9(O)-methano-$\Delta^{6(9\alpha)}$-prostaglandin $I_1$
(65) 19-methyl-20-(1-propenyl)-9(O)-methano-$\Delta^{6(9\alpha)}$-prostaglandin $I_1$
(66) 19,19-dimethyl-20-(1-propenyl)-9(O)-methano-$\Delta^{6(9\alpha)}$-prostaglandin $I_1$
(67) 19-methyl-20-(2-methyl-1-propenyl)-9(O)-methano-$\Delta^{6(9\alpha)}$-prostaglandin $I_1$
(68) 18-methyl-20-(2-methyl-1-propenyl)-9(O)-methano-$\Delta^{6(9\alpha)}$-prostaglandin $I_1$
(69) 18,18-dimethyl-20-(2-methyl-1-propenyl)-9(O)-methano-$\Delta^{6(9\alpha)}$-prostaglandin $I_1$
(70) 20-(1-butenyl)-9(O)-methano-$\Delta^{6(9\alpha)}$-prostaglandin $I_1$
(71) 20-(2-methyl-1-butenyl)-9(O)-methano-$\Delta^{6(9\alpha)}$-prostaglandin $I_1$
(72) 20-(2-ethyl-1-butenyl)-9(O)-methano-$\Delta^{6(9\alpha)}$-prostaglandin $I_1$
(73) 20-methyl-20-butenyl-9(O)-methano-$\Delta^{6(9\alpha)}$-prostaglandin $I_1$
(74) 19-methyl-20-butenyl-9(O)-methano-$\Delta^{6(9\alpha)}$-prostaglandin $I_1$
(75) 19,19-dimethyl-20-butenyl-9(O)-methano-$\Delta^{6(9\alpha)}$-prostaglandin $I_1$
(76) 20-nol-18,19-tetrahydro-9(O)-methano-$\Delta^{6(9\alpha)}$-prostaglandin $I_1$
(77) 18,19-tetrahydro-9(O)-methano-$\Delta^{6(9\alpha)}$-prostaglandin $I_1$
(78) 18,19-tetrahydro-20-methyl-9(O)-methano-$\Delta^{6(9\alpha)}$-prostaglandin $I_1$
(79) 18,19-tetrahydro-20-ethyl-9(O)-methano-$\Delta^{6(9\alpha)}$-prostaglandin $I_1$
(80) 18,19-tetrahydro-20-butyl-9(O)-methano-$\Delta^{6(9\alpha)}$-prostaglandin $I_1$
(81) 18,19-tetrahydro-20-propyl-9(O)-methano-$\Delta^{6(9\alpha)}$-prostaglandin $I_1$
(82) 18,19-tetrahydro-20,20-dimethyl-9(O)-methano-$\Delta^{6(9\alpha)}$-prostaglandin $I_1$
(83) 18,19-tetrahydro-20,20,20-trimethyl-9(O)-methano-$\Delta^{6(9\alpha)}$-prostaglandin $I_1$
(84) 18,19-tetrahydro-20-methyl-20-ethyl-9(O)-methano-$\Delta^{6(9\alpha)}$-prostaglandin $I_1$
(85) 18,19-tetrahydro-20,20-dimethyl-20-ethyl-9(O)-methano-$\Delta^{6(9\alpha)}$-prostaglandin $I_1$
(86) 18,19-tetrahydro-20,20-diethyl-9(O)-methano-$\Delta^{6(9\alpha)}$-prostaglandin $I_1$
(87) 18,19-tetrahydro-20-isopropyl-9(O)-methano-$\Delta^{6(9\alpha)}$-prostaglandin $I_1$
(88) 18,19-tetrahydro-20-t-butyl-9(O)-methano-$\Delta^{6(9\alpha)}$-prostaglandin $I_1$
(89) 18,19-tetrahydro-20-methyl-20-propyl-9(O)-methano-$\Delta^{6(9\alpha)}$-prostaglandin $I_1$
(90) 18,19-tetrahydro-20,20-dimethyl-20-propyl-9(O)-methano-$\Delta^{6(9\alpha)}$-prostaglandin $I_1$
(91) 18,19-tetrahydro-20-(2-methylpropyl)-9(O)-methano-$\Delta^{6(9\alpha)}$-prostaglandin $I_1$
(92) 18,19-tetrahydro-20-(2,2-dimethylpropyl)-9(O)-methano-$\Delta^{6(9\alpha)}$-prostaglandin $I_1$
(93) 18,19-tetrahydro-20-methyl-20-butyl-9(O)-methano-$\Delta^{6(9\alpha)}$-prostaglandin $I_1$
(94) 18,19-tetrahydro-20,20-dimethyl-20-butyl-9(O)-methano-$\Delta^{6(9\alpha)}$-prostaglandin $I_1$
(95) 18,19-tetrahydro-20-(2-methylbutyl)-9(O)-methano-$\Delta^{6(9\alpha)}$-prostaglandin $I_1$
(96) 18,19-tetrahydro-20-(2-ethylbutyl)-9(O)-methano-$\Delta^{6(9\alpha)}$-prostaglandin $I_1$
(97) 18,19-tetrahydro-20-(2,2-dimethylbutyl)-9(O)-methano-$\Delta^{6(9\alpha)}$-prostaglandin $I_1$
(98) 19,20-tetrahydro-9(O)-methano-$\Delta^{6(9\alpha)}$-prostaglandin $I_1$
(99) 19,20-tetrahydro-18-methyl-9(O)-methano-$\Delta^{9(6\alpha)}$-prostaglandin $I_1$
(100) 19,20-tetrahydro-18,20-dimethyl-9(O)-methano-$\Delta^{6(9\alpha)}$-prostaglandin $I_1$
(101) 19,20-tetrahydro-20-methyl-9(O)-methano-$\Delta^{6(9\alpha)}$-prostaglandin $I_1$
(102) 19,20-tetrahydro-20-ethyl-9(O)-methano-$\Delta^{6(9\alpha)}$-prostaglandin $I_1$
(103) 19,20-tetrahydro-20-isopropyl-9(O)-methano-$\Delta^{6(9\alpha)}$-prostaglandin $I_1$
(104) 19,20-tetrahydro-20-t-butyl-9(O)-methano-$\Delta^{6(9\alpha)}$-prostaglandin $I_1$
(105) 19,20-tetrahydro-20-propyl-9(O)-methano-$\Delta^{6(9\alpha)}$-prostaglandin $I_1$
(106) 19,20-tetrahydro-20-(1-methylpropyl)-9(O)-methano-$\Delta^{6(9\alpha)}$-prostaglandin $I_1$
(107) 19,20-tetrahydro-20-(1-ethylpropyl)-9(O)-methano-$\Delta^{6(9\alpha)}$-prostaglandin $I_1$
(108) 19,20-tetrahydro-20-(1,1-dimethylpropyl)-9(O)-methano-$\Delta^{6(9\alpha)}$-prostaglandin $I_1$
(109) 19,20-tetrahydro-20-butyl-9(O)-methano-$\Delta^{6(9\alpha)}$-prostaglandin $I_1$
(110) 19,20-tetrahydro-18-dimethyl-20-butyl-9(O)-methano-$\Delta^{6(9\alpha)}$-prostaglandin $I_1$
(111) 19,20-tetrahydro-20-(1-methylbutyl)-9(O)-methano-$\Delta^{6(9\alpha)}$-prostaglandin $I_1$
(112) 19,20-tetrahydro-20-(1,1-dimethylbutyl)-9(O)-methano-$\Delta^{6(9\alpha)}$-prostaglandin $I_1$
(113) 19,20-tetrahydro-20-(2,2-dimethylbutyl)-9(O)-methano-$\Delta^{6(9\alpha)}$-prostaglandin $I_1$
(114) 19,20-tetrahydro-20-(2-ethylbutyl)-9(O)-methano-$\Delta^{6(9\alpha)}$-prostaglandin $I_1$
(115) 19,20-tetrahydro-18-methyl-20-propyl-9(O)-methano-$\Delta^{6(9\alpha)}$-prostaglandin $I_1$
(116) 20-methylidene-9(O)-methano-$\Delta^{6(9\alpha)}$-prostaglandin $I_1$
(117) 20-methylidene-18-methyl-9(O)-methano-$\Delta^{6(9\alpha)}$-prostaglandin $I_1$
(118) 20-methylidene-20-methyl-9(O)-methano-$\Delta^{6(9\alpha)}$-prostaglandin $I_1$
(119) 20-ethylidene-9(O)-methano-$\Delta^{6(9\alpha)}$-prostaglandin $I_1$
(120) 20-propylidene-9(O)-methano-$\Delta^{6(9\alpha)}$-prostaglandin $I_1$
(121) 20-(2-methylpropylidine)-9(O)-methano-$\Delta^{6(9\alpha)}$-prostaglandin $I_1$
(122) 20-propylidine-19-methyl-9(O)-methano-$\Delta^{6(9\alpha)}$-prostaglandin $I_1$
(123) 20-(2,2-dimethylpropylidine)-9(O)-methano-$\Delta^{6(9\alpha)}$-prostaglandin $I_1$
(124) 20-propylidine-19,19-dimethyl-9(O)-methano-$\Delta^{6(9\alpha)}$-prostaglandin $I_1$
(125) 20-butylidine-9(O)-methano-$\Delta^{6(9\alpha)}$-prostaglandin $I_1$
(126) 20-butylidine-18-methyl-9(O)-methano-$\Delta^{6(9\alpha)}$-prostaglandin $I_1$
(127) 20-butylidine-18,18-dimethyl-9(O)-methano-$\Delta^{6(9\alpha)}$-prostaglandin $I_1$
(128) 20-butylidine-18,18-dimethyl-9(O)-methano-$\Delta^{6(9\alpha)}$-prostaglandin $I_1$
(129) 20-butylidine-19,19-dimethyl-9(O)-methano-$\Delta^{6(9\alpha)}$-prostaglandin $I_1$
(130) 20-butylidine-19-methyl-9(O)-methano-$\Delta^{6(9\alpha)}$-prostaglandin $I_1$
(131) 20-(2-methylbutylidine)-9(O)-methano-$\Delta^{6(9\alpha)}$-prostaglandin $I_1$
(132) 20-(2-ethylbutylidine)-9(O)-methano-$\Delta^{6(9\alpha)}$-prostaglandin $I_1$
(133) 20-(3-methylbutylidine)-9(O)-methano-$\Delta^{6(9\alpha)}$-prostaglandin $I_1$ (134) 20-(3,3-dimethylbutylidine)-9(O)-methano-$\Delta^{6(9\alpha)}$-prostaglandin $I_1$
(135) 20-(3,3-dimethylbutylidine)-9(O)-methano-$\Delta^{6(9\alpha)}$-prostaglandin $I_1$
(136) 20-ethynyl-9(O)-methano-$\Delta^{6(9\alpha)}$-prostaglandin $I_1$
(137) 20-ethynyl-18-methyl-9(O)-methano-$\Delta^{6(9\alpha)}$-prostaglandin $I_1$
(138) 20-ethynyl-19-methyl-9(O)-methano-$\Delta^{6(9\alpha)}$-prostaglandin $I_1$
(139) 20-ethynyl-19,19-dimethyl-9(O)-methano-$\Delta^{6(9\alpha)}$-prostaglandin $I_1$
(140) 20-ethynyl-20-methyl-9(O)-methano-$\Delta^{6(9\alpha)}$-prostaglandin $I_1$
(141) 20-ethynyl-20,20-trimethyl-9(O)-methano-$\Delta^{6(9\alpha)}$-prostaglandin $I_1$
(142) 20-(1-propynyl)-9(O)-methano-$\Delta^{6(9\alpha)}$-prostaglandin $I_1$
(143) 20-(1-propynyl)-18-methyl-9(O)-methano-$\Delta^{6(9\alpha)}$-prostaglandin $I_1$
(144) 20-(1-propynyl)-19-methyl-9(O)-methano-$\Delta^{6(9\alpha)}$-prostaglandin $I_1$
(145) 20-(1-propynyl)-19,19-dimethyl-9(O)-methano-$\Delta^{6(9\alpha)}$-prostaglandin $I_1$
(146) 20-(1-propynyl)-20-methyl-9(O)-methano-$\Delta^{6(9\alpha)}$-prostaglandin $I_1$
(147) 20-(1-propynyl)-20,20-dimethyl-9(O)-methano-$\Delta^{6(9\alpha)}$-prostaglandin $I_1$
(148) 20-(1-butynyl)-9(O)-methano-$\Delta^{6(9\alpha)}$-prostaglandin $I_1$
(149) 20-(1-butynyl)-18-methyl-9(O)-methano-$\Delta^{6(9\alpha)}$-prostaglandin $I_1$
(150) 20-(1-butynyl)-19-methyl-9(O)-methano-$\Delta^{6(9\alpha)}$-prostaglandin $I_1$
(151) 20-(1-butynyl)-19,19-dimethyl-9(O)-methano-$\Delta^{6(9\alpha)}$-prostaglandin $I_1$
(152) 20-(1-butynyl)-20-methyl-9(O)-methano-$\Delta^{6(9\alpha)}$-prostaglandin $I_1$
(153) 20-(3-methyl-1-butynyl)-9(O)-methano-$\Delta^{6(9\alpha)}$-prostaglandin $I_1$
(154) 20-(3,3-dimethyl-1-butynyl)-9(O)-methano-$\Delta^{6(9\alpha)}$-prostaglandin $I_1$
(155) 20-(2-butynyl)-9(O)-methano-$\Delta^{6(9\alpha)}$-prostaglandin $I_1$
(156) 20-(2-propynyl)-18-methyl-9(O)-methano-$\Delta^{6(9\alpha)}$-prostaglandin $I_1$
(157) 20-(2-propynyl)-18,18-dimethyl-9(O)-methano-$\Delta^{6(9\alpha)}$-prostaglandin $I_1$
(158) 20-(2-propynyl)-19-methyl-9(O)-methano-$\Delta^{6(9\alpha)}$-prostaglandin $I_1$
(159) 20-(2-propynyl)-19,19-dimethyl-9(O)-methano-$\Delta^{6(9\alpha)}$-prostaglandin $I_1$
(160) 20-(2-propynyl)-20-methyl-9(O)-methano-$\Delta^{6(9\alpha)}$-prostaglandin $I_1$
(161) 20-(1-methyl-2-propynyl)-9(O)-methano-$\Delta^{6(9\alpha)}$-prostaglandin $I_1$
(162) 20-(1,1-dimethyl-2-propynyl)-9(O)-methano-$\Delta^{6(9\alpha)}$-prostaglandin $I_1$
(163) 20-(2-butynyl)-9(O)-methano-$\Delta^{6(9\alpha)}$-prostaglandin $I_1$
(164) 20-(2-butynyl)-18-methyl-9(O)-methano-$\Delta^{6(9\alpha)}$-prostaglandin $I_1$
(165) 20-(2-butynyl)-18,18-dimethyl-9(O)-methano-$\Delta^{6(9\alpha)}$-prostaglandin $I_1$
(166) 20-(2-butynyl)-19,19-dimethyl-9(O)-methano-$\Delta^{6(9\alpha)}$-prostaglandin $I_1$
(167) 20-(2-butynyl)-20,20-dimethyl-9(O)-methano-$\Delta^{6(9\alpha)}$-prostaglandin $I_1$
(168) 20-(1-methyl-2-butynyl)-9(O)-methano-$\Delta^{6(9\alpha)}$-prostaglandin $I_1$
(169) 20-(1,1-dimethyl-2-butynyl)-9(O)-methano-$\Delta^{6(9\alpha)}$-prostaglandin $I_1$
(170) 20-(3-butynyl)-9(O)-methano-$\Delta^{6(9\alpha)}$-prostaglandin $I_1$
(171) 20-(3-butynyl)-18-methyl-9(O)-methano-$\Delta^{6(9\alpha)}$-prostaglandin $I_1$
(172) 20-(3-butynyl)-18,18-dimethyl-9(O)-methano-$\Delta^{6(9\alpha)}$-prostaglandin $I_1$
(173) 20-(3-butynyl)-20-methyl-9(O)-methano-$\Delta^{6(9\alpha)}$-prostaglandin $I_1$
(174) 20-(1-methyl-3-butynyl)-9(O)-methano-$\Delta^{6(9\alpha)}$-prostaglandin $I_1$
(175) 20-(2-methyl-3-butynyl)-9(O)-methano-$\Delta^{6(9\alpha)}$-prostaglandin $I_1$
(176) 20-(2,2-dimethyl-3-butynyl)-9(O)-methano-$\Delta^{6(9\alpha)}$-prostaglandin $I_1$
(177) 20-(1,1-dimethyl-3-butynyl)-9(O)-methano-$\Delta^{6(9\alpha)}$-prostaglandin $I_1$
(178) 16,17,18,19,20-pentanol-15-cyclopentyl-9(O)-methano-$\Delta^{6(9\alpha)}$-prostaglandin $I_1$
(179) 16,17,18,19,20-pentanol-15-cyclohexyl-9(O)-methano-$\Delta^{6(9\alpha)}$-prostaglandin $I_1$
(180) 16,17,18,19,20-pentanol-15-(2-chlorohexyl-9(O)-methano-$\Delta^{6(9\alpha)}$-prostaglandin $I_1$
(181) 16,17,18,19,20-pentanol-15-(3-trifluoromethylcyclohexyl)- 9(O)-methano-$\Delta^{6(9\alpha)}$-prostaglandin $I_1$
(182) 17-ethoxy-9-(O) -methano-$\Delta^{6(9\alpha)}$-prostaglandin $I_1$
(183) An ethyl ester of (1) to (182)
(184) A butyl ester of (1) to (182)
(185) A sodium salt of (1) to (182)
(186) A potassium salt of (1) to (182)
(187) An ammonium salt of (1) to (182)
but the invention is not limited to the same.

The prostacyclin of the above formula (I) is easily produced by known methods. These processes of production are described in, for example, Japanese Unexamined Patent Publication (Kokai) Nos. 59-210044, 61-197518, etc.

It became clear that there was a powerful skin ulcer treatment activity upon use of the prostacyclin of the formula (I) as an external skin treatment agent composition, in particular, a transdermal agent. For example, application of an ointment containing prostacyclin of formula (I) to a diseased location, that is, a skin ulcer (rabbit decubitus ulcer lesion model) prepared by applying pressure to the skin on the back of a rabbit, exhibited a therapeutic effect. Further, the amount of the blood flow of the skin containing the prostacyclin of formula (I) was remarkably increased.

The above active compound may be used as an external skin treatment agent, in particular, an agent for treatment of skin ulcers, for example, decubitus ulcers, scald ulcers, angiopathic ulcers, diabetic ulcers, peripheral circulatory disorders, ulcers accompanying collagen diseases, and other ulcers.

As the preparation of the transdermal agent composition having as an active ingredient the prostacyclin of the formula (I), mention may be made of an ointment, cream, lotion, liquid, etc.

The concentration of the active ingredient in the external skin treatment agent composition according to the present invention is not particularly limited, but preferably is $10^{-6}$ to $10^{-1}$% by weight, more preferably $10^{-5}$ to $10^{-2}$% by weight, in terms of the total composition.

As the carrier (base) of the external skin treatment agent of the present invention, mention may be made, for example, of castor oil, olive oil, sesame oil, safflower oil, and other fatty oils, lanolin, white, yellow, or hydrophilic vaselin, beeswax, bleached beeswax, spermaceti wax, paraffin wax, and other waxes, oleyl alcohol, isostearyl alcohol, octyl dodeca alcohol, hexyl decanol, and other higher alcohols, glycerin, diglycerin, ethylene glycerol, propylene glycol, sorbitol, 1,3-butanediol, and other glycols. Further, as the solubilizing agent of the prostacyclin, use may be made of ethanol, dimethylsulfoxide, polyethylene glycol, etc. Also, in accordance with need, use may also be made of antioxidants such as paraoxyl benzoic acid esters, sodium benzoate, salicylic acid, sorbic acid, boric acid, and other preservatives, dibutylhydroxytoluene, and the like. In addition, suitable amounts of oil components, surfactants, water, moisture retainers, thickeners, fragrances, dyes, etc. may be added to an extent not impairing the effect of the present invention.

To promote the transdermal absorption of prostacyclin, an absorption promotor such as diisopropyl adipate, diethyl sebacate, ethyl caproate, ethyl laurate, etc. may be added.

An ointment may be produced by an ordinary method. For example, mention may be made of the method of adding a fatty oil to a prostacyclin, dissolving the same in it, adding this solution to a separately warmed and melted wax, homogeneously mixing them, and then cooling. A cream can be produced by an ordinary method. For example, mention may be made of the method of heating and melting a prostacyclin and an oil phase component (fatty oil, surfactant), adding heated water to this, adding a mixture of glycols, while stirring, and then cooling.

Aside from these preparations, mention may be made of preparations such as lotions, liquids, pastes, cataplasms and aerosols. The preparations may be produced by ordinary methods.

The dosage of the prostacyclin differs depending on the type of the compound, the state of the disease, etc., but the medication is usually administered in an amount of from about 1 ng to about 1 mg/site. Accordingly, the amount of the prostacyclin contained in the transdermal medication is determined by the dosage.

The transdermal medication having a prostacyclin as an active ingredient according to the present invention, as mentioned earlier, is applied locally to the skin, so is limited in location of action and therefore can exhibit a pharmacological activity just at a specific site.

According to the present invention, it is clear that prostaglandin of the formula (I) exhibits a therapeutic effect on skin ulcers. Note that the external skin ointment of the present invention was not observed to particularly have acute toxicity.

EXAMPLES

The present invention will be explained in further detail by Examples.

EXAMPLE 1

One hundred grams of an ointment having the following composition were prepared.

| | |
|---|---|
| 9(O)-methano-$\Delta^{6(9\alpha)}$-prostaglandin $I_1$ | 0.05 mg |
| Beeswax | 33 g |
| Vegetable oil | 77 g |

EXAMPLE 2

One hundred grams of a cream having the following composition were prepared.

| | |
|---|---|
| 9(O)-methano-$\Delta^{6(9\alpha)}$-prostaglandin $I_1$ | 0.05 mg |
| Beeswax | 10 g |
| Paraffin wax | 6 g |
| Lanolin | 3 g |
| Isopropyl myristate | 6 g |
| Squalane | 8 g |
| Liquid paraffin | 25 g |
| Sorbitan monostearate | 4 g |
| Polyoxyethylenesorbitan monostearate | 2 g |
| Preservative | q.s. |
| Propylene glycol | 2 g |
| Water | 30 g |

EXAMPLE 3

Transdermal therapeutic effect on skin ulcers by 9(O)-methano-$\Delta^{6(9\alpha)}$-prostaglandin $I_1$ Coating an ointment containing 9(O)-methano-$\Delta^{6(9\alpha)}$-prostaglandin $I_1$ to a skin ulcer (rabbit decubitus ulcer lesion model) prepared by applying pressure to the skin on the back of a rabbit exhibited a therapeutic effect. That is, the skin areas on the III trochanters on the left and right of Japanese white male rabbits fasted for 15 to 20 days were dipilated and pressure was applied on those portions to prepare skin ulcers. Subsequently, an ointment containing prostacyclin was coated on the right lesions of the subjects and vaseline on the left lesions once a day in amounts of 0.02 g/site. The curing process of the lesions was found by the ratio of area by the following equation in accordance with the method of Fukawa (Applied Pharmacology, 7, 1305, 1973).

Ratio of area (%)=(long length×short length of ulcer area) (day observed)/(long length×short length of ulcer area) (day ulcer prepared)×100.

The results are shown in Table 1. The lesions coated with the ointment containing the prostacyclin of the formula (I) shrank significantly compared with the control sites on day 3, 5, and 7 and a therapeutic effect was confirmed.

TABLE 1

| Concentration | | Ratio of area of wound (%) | | | | |
|---|---|---|---|---|---|---|
| | | 0 | 3 | 5 | 7 | 10 (days) |
| 0.032 μg/g | R[a)] | 100 | 62.31 ± 5.82 | 38.51 ± 5.98 | 16.41 ± 2.22 | 8.00 ± 1.90 |
| | | (N = 11) | (N = 11) | (N = 11) | (N = 11) | (N = 11) |
| | L[b)] | 100 | 72.43 ± 6.37 | 41.02 ± 7.04 | 20.45 ± 3.27 | 8.85 ± 2.26 |
| 0.16 μg/g | R[a)] | 100 | 62.52 ± 6.69 | 37.86 ± 6.57 | 20.45 ± 4.78* | 15.18 ± 6.85 |
| | | (N = 11) | (N = 11) | (N = 11) | (N = 11) | (N = 11) |
| | L[b)] | 100 | 83.28 ± 7.87 | 59.18 ± 8.74 | 35.58 ± 4.39 | 24.27 ± 3.23 |
| 0.8 μg/g | R[a)] | 100 | 60.70 ± 6.15* | 35.24 ± 6.18* | 18.02 ± 3.56** | 8.31 ± 2.01 |
| | | (N = 11) | (N = 11) | (N = 11) | (N = 11) | (N = 11) |

TABLE 1-continued

| Concentration | Ratio of area of wound (%) | | | | |
| --- | --- | --- | --- | --- | --- |
| | 0 | 3 | 5 | 7 | 10 (days) |
| L[b] | 100 | 82.16 ± 4.61 | 54.35 ± 5.26 | 35.79 ± 3.88 | 16.41 ± 4.08 |

Figures of ratio of area of wound are mean values ± standard error.
N: Number of animals used
[a]Right side: specimen applied
[b]Left side (control): vaseline applied
*5% significance in comparison with left side (control)
**1% significance in comparison with left side (control)

EXAMPLE 4

Transdermal action of increasing amount of blood flow of skin by 9(O)-methano-$\Delta^{6(9\alpha)}$-prostaglandin $I_1$ An ointment containing 9(O)-methano-$\Delta^{6(9\alpha)}$-prostaglandin $I_1$ remarkably increased the amount of the blood flow of the skin at the sites of administration of hairless rats as shown in FIG. 1.

The external skin treatment agent composition having the prostacyclin of formula (I) of the present invention as its active ingredient exhibited a superior therapeutic effect.

We claim:

1. An external skin ulcer treatment agent composition containing an active ingredient comprising a prostacyclin, and/or its optical isomer, having the formula (I):

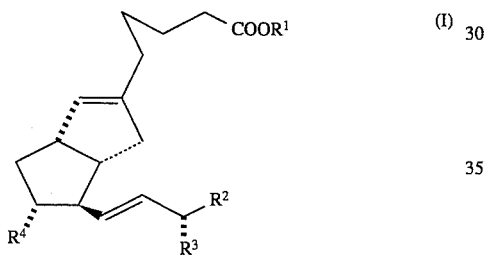

(wherein, $R^1$ is a hydrogen atom, a straight chain or branched alkyl group of $C_1$ to $C_{10}$, or one equivalent of cations, $R^2$ is $-(CH_2)_2R^{21}$ or a substitutable $C_3$ to $C_{10}$ cycloalkyl group, where $R^{21}$ is a substitutable $C_1$ to $C_{10}$ straight chain or branched alkyl group or substitutable $C_2$ to $C_{10}$ straight chain or branched alkenyl group or alkynyl group, and $R^3$ and $R^4$ are independently a hydroxyl group or formula:

(wherein, $R^5$ is a $C_1$ to $C_5$ straight chain or branched alkyl group)) and a carrier.

2. An external skin ulcer treatment agent composition as claimed in claim 1, wherein the $R^1$ in formula (I) is a hydrogen atom or a methyl group.

3. The external skin ulcer treatment agent composition claimed in claim 1, wherein $R^1$ in formula (I) is a hydrogen atom or a methyl group, and $R^2$ in formula (I) is a pentyl group.

4. The external skin ulcer treatment agent composition claimed in claim 1, wherein $R^2$ in formula (I) is a pentyl group.

5. The external skin ulcer treatment agent composition claimed in claim 1, wherein the external skin treatment agent in formula (I) is a transdermal agent.

6. The external skin ulcer treatment agent composition claimed in claim 1, wherein $R^1$ in formula (I) is a hydrogen atom or a methyl group, and the external skin treatment agent in formula (I) is a transdermal agent.

7. The external skin ulcer treatment agent composition claimed in claim 1, wherein $R^2$ in formula (I) is a pentyl group, and the external skin treatment agent in formula (I) is a transdermal agent.

8. The external skin ulcer treatment agent composition claimed in claim 1, wherein $R^1$ in formula (I) is a hydrogen atom or a methyl group, and $R^2$ in formula (I) is a pentyl group, and the external skin treatment agent in formula (I) is a transdermal agent.

9. The external skin ulcer treatment agent composition claimed in claim 1, wherein the external skin treatment agent is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

10. The external skin ulcer treatment agent composition claimed in claim 1, wherein $R^1$ in formula (I) is a hydrogen atom or a methyl group, and the external skin treatment agent is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

11. The external skin ulcer treatment agent composition claimed in claim 1, wherein $R^2$ in formula (I) is a pentyl group, and the external skin treatment agent is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

12. The external skin ulcer treatment agent composition claimed in claim 1, wherein $R^1$ in formula (I) is a hydrogen atom or a methyl group, $R^2$ in formula (I) is a pentyl group, and the external skin treatment agent is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

13. The external skin ulcer treatment agent composition claimed in claim 1, wherein the external skin treatment agent in formula (I) is a transdermal agent and is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

14. The external skin ulcer treatment agent composition claimed in claim 1, wherein $R^1$ in formula (I) is a hydrogen atom or a methyl group, and the external skin treatment agent in formula (I) is a transdermal agent and is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

15. The external skin ulcer treatment agent composition claimed in claim 1, wherein $R^2$ in formula (I) is a pentyl group, and the external skin treatment agent in formula (I) is a transdermal agent and is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

16. The external skin ulcer treatment agent composition claimed in claim 1, wherein $R^1$ in formula (I) is a hydrogen atom or a methyl group, and $R^2$ in formula (I) is a pentyl group, and the external skin treatment agent in formula (I) is a transdermal agent and is an agent for treatment of ulcers wherein said ulcers are selected from the group consisting of decubitus ulcers, scald ulcers, angiopathic ulcers, diabetic ulcers, peripheral circulatory disorders and ulcers accompanying collagen diseases.

17. The external skin ulcer treatment agent composition claimed in claim 1, comprising $10^{-6}$ to $10^{-1}\%$ by weight of the active ingredient.

18. The external skin ulcer treatment agent composition claimed in claim 1, comprising $10^{-5}$ to $10^{-2}\%$ by weight of the active ingredient.

19. A method of treating external skin ulcers comprising administering to a patient in need of such treatment an anti-external skin ulcer effective amount of a pharmaceutical composition comprising an active ingredient wherein the active ingredient comprises a prostacyclin, and/or its optical isomer, having the formula (I):

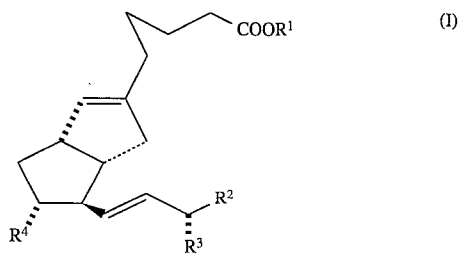

(wherein $R^1$ is a hydrogen atom, a straight chain or branched alkyl group of $C_1$ to $C_{10}$, or one equivalent of cations, $R^2$ is $(CH_2)R^{21}$ or a substitutable $C_3$ to $C_{10}$ cycloalkyl group, where $R^{21}$ is a substitute $C_1$ to $C_{10}$ straight chain or branched alkyl group or substitutable $C_2$ to $C_{10}$ straight chain or branched alkenyl group or alkynyl group, and $R^3$ and $R^4$ are independently a hydroxyl group or formula:

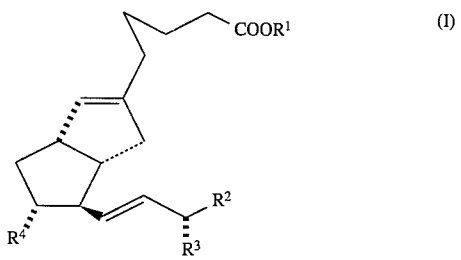

(wherein, $R^5$ is a $C_1$ to $C_5$ straight chain or branched alkyl group)) and a carrier.

* * * * *